(12) United States Patent
Bachovchin

(10) Patent No.: US 7,569,546 B2
(45) Date of Patent: Aug. 4, 2009

(54) APOLIPOPROTEIN A1 MIMETICS AND USES THEREOF

(75) Inventor: William W. Bachovchin, Cambridge, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 11/182,490

(22) Filed: Jul. 15, 2005

(65) Prior Publication Data

US 2006/0069030 A1 Mar. 30, 2006

Related U.S. Application Data

(60) Provisional application No. 60/588,722, filed on Jul. 16, 2004.

(51) Int. Cl.
*A61K 38/10* (2006.01)
*C07K 7/08* (2006.01)
(52) U.S. Cl. .......................... 514/13; 530/326
(58) Field of Classification Search ........................ None
See application file for complete search history.

(56) References Cited

U.S. PATENT DOCUMENTS

| | | | |
|---|---|---|---|
| 6,319,498 B1 * | 11/2001 | Findeis et al. ............... | 424/94.3 |
| 6,933,279 B2 * | 8/2005 | Fogelman et al. ............. | 514/13 |
| 2003/0045460 A1 | 3/2003 | Fogelman et al. | |
| 2003/0224997 A1 * | 12/2003 | Hinman et al. ................. | 514/14 |
| 2006/0205669 A1 * | 9/2006 | Fogelman et al. ............. | 514/16 |
| 2006/0234908 A1 * | 10/2006 | Fogelman ..................... | 514/2 |

OTHER PUBLICATIONS

Fischer. The Design, Synthesis and Application of Stereochemical and Directional Peptide Isomers: A Critical Review. Current Protein and Peptide Science. 2003, vol. 4, pp. 339-356.*
Navab, N. et al., "Oral Administration of an Apo A-I Mimetic Peptide Synthesized From D-Amino Acids Dramatically Reduces Atherosclerosis in Mice Independent of Plasma Cholesterol", *Circuilation*, 105(3):290-292 (Jan. 22, 2002).
International Search Report dated May 18, 2006.

* cited by examiner

*Primary Examiner*—Jeffrey E Russel
(74) *Attorney, Agent, or Firm*—Foley Hoag, LLP

(57) ABSTRACT

The present invention provides peptidomimetics derived from Apolipoprotein A-I, which is useful for beneficially influencing lipid parameters and/or plasma cholesterol levels. The invention also provides pharmaceutical compositions and methods of treatment for elevated levels of plasma cholesterol.

5 Claims, 7 Drawing Sheets

L4F: Ac-Asp-Trp-Phe-Lys-Ala-Phe-Tyr-Asp-Lys-Val-Ala-Glu-Lys-Phe-Lys-Glu-Ala-Phe-NH$_2$ (SEQ ID. No. 1)

L Configuration

D4F: Ac-Asp-Trp-Phe-Lys-Ala-Phe-Tyr-Asp-Lys-Val-Ala-Glu-Lys-Phe-Lys-Glu-Ala-Phe-NH$_2$

D Configuration

Rev D4F: Ac-Phe-Ala-Glu-Lys-Phe-Lys-Glu-Ala-Val-Lys-Asp-Tyr-Phe-Ala-Lys-Phe-Trp-Asp-NH$_2$ (SEQ ID. No. 2)

Reverse D Configuration

L4F:   Ac-Asp-Trp-Phe-Lys-Ala-Phe-Tyr-Asp-Lys-Val-Ala-Glu-Lys-Phe-Lys-Glu-Ala-Phe-NH$_2$ (SEQ ID. No. 1)  | L Configuration |

D4F:   Ac-Asp-Trp-Phe-Lys-Ala-Phe-Tyr-Asp-Lys-Val-Ala-Glu-Lys-Phe-Lys-Glu-Ala-Phe-NH$_2$  | D Configuration |

Rev D4F: Ac-Phe-Ala-Glu-Lys-Phe-Lys-Glu-Ala-Val-Lys-Asp-Tyr-Phe-Ala-Lys-Phe-Trp-Asp-NH$_2$ (SEQ ID. No. 2)  | Reverse D Configuration |

Figure 1

SEQUENCE LISTING

```
<160> NUMBER OF SEQ ID NOS: 3

<210> SEQ ID NO 1
<211> LENGTH: 18
<212> TYPE: PRT
<213> ORGANISM: Artificial Sequence
<220> FEATURE:
<223> OTHER INFORMATION: Apo A-I mimetic peptide
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 1

Asp Trp Phe Lys Ala Phe Tyr Asp Lys Val Ala Glu Lys Phe Lys Glu
 1               5                  10                  15

Ala Phe

<210> SEQ ID NO 2
<211> LENGTH: 18
<212> TYPE: PRT
<213> ORGANISM: Artificial Sequence
<220> FEATURE:
<223> OTHER INFORMATION: Apo A-I mimetic peptide
```

```
<220> FEATURE:
<221> NAME/KEY: VARIANT
<222> LOCATION: 1, 5, 13, 16
<223> OTHER INFORMATION: Xaa = D-Phe
<220> FEATURE:
<221> NAME/KEY: VARIANT
<222> LOCATION: 2, 8, 14
<223> OTHER INFORMATION: Xaa = D-Ala
<220> FEATURE:
<221> NAME/KEY: VARIANT
<222> LOCATION: 3, 7
<223> OTHER INFORMATION: Xaa = D-Glu
<220> FEATURE:
<221> NAME/KEY: VARIANT
<222> LOCATION: 4, 6, 10, 15
<223> OTHER INFORMATION: Xaa = D-Lys
<220> FEATURE:
<221> NAME/KEY: VARIANT
<222> LOCATION: 11, 18
<223> OTHER INFORMATION: Xaa = D-Asp
<220> FEATURE:
<221> NAME/KEY: VARIANT
<222> LOCATION: (9)...(9)
<223> OTHER INFORMATION: Xaa = D-Val
<220> FEATURE:
<221> NAME/KEY: VARIANT
<222> LOCATION: (12)...(12)
<223> OTHER INFORMATION: Xaa = D-Tyr
<220> FEATURE:
<221> NAME/KEY: VARIANT
<222> LOCATION: (17)...(17)
<223> OTHER INFORMATION: Xaa = D-Trp
<220> FEATURE:
<221> NAME/KEY: ACETYLATION
<222> LOCATION: (1)...(1)
<220> FEATURE:
<221> NAME/KEY: AMIDATION
<222> LOCATION: (18)...(18)

<400> SEQUENCE: 2

Xaa Xaa Xaa Xaa Xaa Xaa Xaa Xaa Xaa Xaa Xaa Xaa Xaa Xaa Xaa
 1               5                   10                  15

Xaa Xaa

<210> SEQ ID NO 3
<211> LENGTH: 18
<212> TYPE: PRT
<213> ORGANISM: Artificial Sequence
<220> FEATURE:
<223> OTHER INFORMATION: Apo A-I mimetic peptide
<220> FEATURE:
<221> NAME/KEY: VARIANT
<222> LOCATION: 1, 5, 13, 16
<223> OTHER INFORMATION: Xaa = D-Phe
<220> FEATURE:
<221> NAME/KEY: VARIANT
<222> LOCATION: 2, 8, 14
<223> OTHER INFORMATION: Xaa = D-Ala
<220> FEATURE:
<221> NAME/KEY: VARIANT
<222> LOCATION: 3, 7
<223> OTHER INFORMATION: Xaa = D-Glu
<220> FEATURE:
<221> NAME/KEY: VARIANT
<222> LOCATION: 4, 6, 10, 15
<223> OTHER INFORMATION: Xaa = D-Lys
<220> FEATURE:
<221> NAME/KEY: VARIANT
<222> LOCATION: 11, 18
<223> OTHER INFORMATION: Xaa = D-Asp
<220> FEATURE:
<221> NAME/KEY: VARIANT
<222> LOCATION: (9)...(9)
<223> OTHER INFORMATION: Xaa = D-Val
<220> FEATURE:
<221> NAME/KEY: VARIANT
```

```
-continued

<222> LOCATION: (12)...(12)
<223> OTHER INFORMATION: Xaa = D-Tyr
<220> FEATURE:
<221> NAME/KEY: VARIANT
<222> LOCATION: (17)...(17)
<223> OTHER INFORMATION: Xaa = D-Trp

<400> SEQUENCE: 3

Xaa Xaa Xaa Xaa Xaa Xaa Xaa Xaa Xaa Xaa Xaa Xaa Xaa Xaa Xaa Xaa
 1               5                   10                  15

Xaa Xaa
```

APOLIPOPROTEIN A1 MIMETICS AND USES THEREOF

RELATED APPLICATION

This application claims the benefit of U.S. Provisional Application No. 60/588,722, filed Jul. 16, 2004. The entire contents of this application are incorporated herein by reference.

BACKGROUND OF THE INVENTION

Vascular diseases, such as cardiovascular, peripheral vascular and cerebral vascular, relating to or arising from lipid disorders, are a leading cause of death and disability in the developed world, particularly afflicting the elderly. Such diseases are a major cause of death in the affluent countries including the United States, where cardiovascular diseases are the cause of almost one million fatalities each year, more than one half of all deaths; almost 5 million persons afflicted with cardiovascular disease are hospitalized each year.

Arteriosclerosis refers to any group of diseases that are characterized by thickening and loss of elasticity in arterial walls. Of these diseases, atherosclerosis, the most common form of vascular disease, and coronary artery diseases have the most significant impact. Normally, the interior surface of the blood vessel is relatively smooth, allowing easy passage of the blood. In atherosclerosis, a common form of vascular disease, deposits of yellowish plaques (atheromas) containing cholesterol, fatty material, calcium, and lipid-filled macrophages are formed within the intima and inner media of large and medium-sized arteries. The plaque causes blockage of the blood vessel, facilitating clotting and leading to insufficient blood supply to critical body organs, which results in organ failures including heart attack, stroke, or kidney failure, and causing hypertension. Atherosclerosis underlies most coronary artery disease.

The very earliest phase of the development of atherosclerotic lesions (the fatty streak) involves the entry of monocytes into the subendothelial regions of the blood vessels. At the same time, low-density lipoprotein cholesterol ("LDL") is retained in the subendothelial regions and is oxidized, causing these monocytes, now differentiated into macrophages, to uptake the oxidatively modified LDL, and stay localized. Such macrophages, or foam cells, increase in the size and their subsequent death and secretion of fibrous elements from the vascular smooth muscle cells ("VSMC") contribute to the formation of the plaque. Atherosclerosis can be considered a hyperproliferative disease, wherein some of the normal VSMC in the artery wall become abnormally proliferative, and concurrently invading and spreading into the inner vessel lining, blocking blood flow and making that vessel abnormally susceptible to being completely blocked by local blood clotting. Such complete blockage may result in the death of the tissue served by that artery.

While elevation of the LDL level is generally unwanted and is considered detrimental to one's health, elevation of the HDL level is considered to be protective against atherosclerosis. HDL cholesterol is often referred to as "good" cholesterol since the negative association between serum HDL concentration and coronary heart disease is at least as strong as the positive association between low density lipoprotein (LDL) and coronary heart disease. Apolipoproteins A-I ("Apo A-I") and A2 are the major apoprotein constituents of HDL, and have been considered to be anti-atherogenic due to their abilities to transport cholesterol from arteries to the liver for catabolism and excretion. See Furchart, J. and Ailhaud, G. (1992) *Clin. Chem.* 38:793-797.

Treatment of atherosclerosis includes management and reduction of the LDL cholesterol using drugs that are designed to inhibit cholesterol synthesis such as HMG-CoA reductase inhibitors (statins), nicotinic acid, bile salt sequestrants, or fibric acid derivatives. These pharmaceutical agents, however, are not without significant side effects. Statins are known to show various degrees of myotoxicity (Rosenson, (2004) *Am. J. Med.* 116(6):408-16), and nicotinic acid commonly induces vasodilatory effects. Fibrates are associated with a number of adverse effects, including liver enzyme elevations, gastrointestinal side effects and rhabdomyolysis (Muscari et al. (2002) *Cardiology* 97(3): 115-21).

Several Class A amphipathic helical peptide analogs of Apo A-I, which is derived from Apo A-I's eight tandem repeating 22-mer sequence, (Apo A-I mimetic peptides) have been shown to be effective against atherosclerotic development. The C-terminal portion of Apo A-I (residues 193 to 243) is thought to be actively involved in protein-lipid interactions. Apo A-I mimetic peptides enhance the ability of high-density lipoprotein (HDL) to protect low-density lipoprotein (LDL) from oxidation and remove seeding molecules from LDL. However, it is not clearly understood whether Apo A-I mimetic peptides protect LDL against oxidation independent of HDL-mediated mechanisms. Such peptides are generally rapidly degraded in vivo.

It has been previously shown that L-4F, an 18 L-amino acid-containing mimetic peptide, and its D-amino acid analog D-4F, block LDL oxidation and LDL-induced monocyte chemotactic activity. Furthermore, D-4F has been shown to be stable upon oral administration, resulting in almost 80% reduction of atherosclerotic lesions in LDL receptor-null mice. Navab et al., (2002) *Circulation* 105:290-292. L-4F and D-4F have a primary amino acid sequence Ac-D-W-F-K-A-F-Y-D-K-V-A-E-K-F-K-E-A-F-NH$_2$, (SEQ ID NO:1). The 18-mer has a potential to form a class A amphipathic helical structure (Segrest et al. (1974) *FEBS Lett.* 38:247-253). L-4F inhibits LDL and phospholipid oxidation through mechanisms independent of HDL-mediated processes.

Nevertheless, there is still a need for improved pharmaceutical agents to treat, prevent, or alter the progress of vascular disorders having a lipid based etiology, such as atherosclerosis, and generally to dyslipidemia, elevated cholesterol or decreased HDL.

BRIEF SUMMARY OF THE INVENTION

The present invention provides peptidomimetics of peptides derived from Apolipoprotein A-I ("Apo A-I"), which are useful for beneficially influencing the plasma cholesterol levels and vascular diseases, such as through altering lipid parameters. In certain embodiments, the peptidomimetic has a substantially similar three-dimensional conformation as a peptide comprising a D-amino acid sequence F-A-E-K-F-K-E-A-V-K-D-Y-F-A-K-F-W-D (SEQ ID NO:3). The compounds of the present invention can be advantageously prophylactically administered to a patient at risk of or showing the symptoms of vascular diseases of lipid etiology such as atherosclerosis, hypercholesterolemia, hyperlipidemia, PAD, CHD and cerebral vascular diseases.

The compounds of present invention are peptidomimetics, in particular amino acid polymers in retro-inverso configuration.

The invention includes the use of peptidomimetics disclosed herein as research tools, such as in determining the anti-atherosclerotic potential of other compounds, investigating lipoprotein-receptor interactions in animals and animal models, and elucidating the mechanisms of lipid metabolism, including identifying animal models for lipid metabolism studies.

The invention also includes the use of the peptidomimetics disclosed in medicine. In addition, the invention includes the use of the peptidomimetics disclosed herein in the manufacture of a medicament for treating a disease or condition disclosed herein.

BRIEF DESCRIPTION OF THE FIGURES

FIG. 1 depicts the peptides and peptidomimetic derived from Apo A-I.

DETAILED DESCRIPTION OF THE INVENTION

I. Overview

Figure 2:
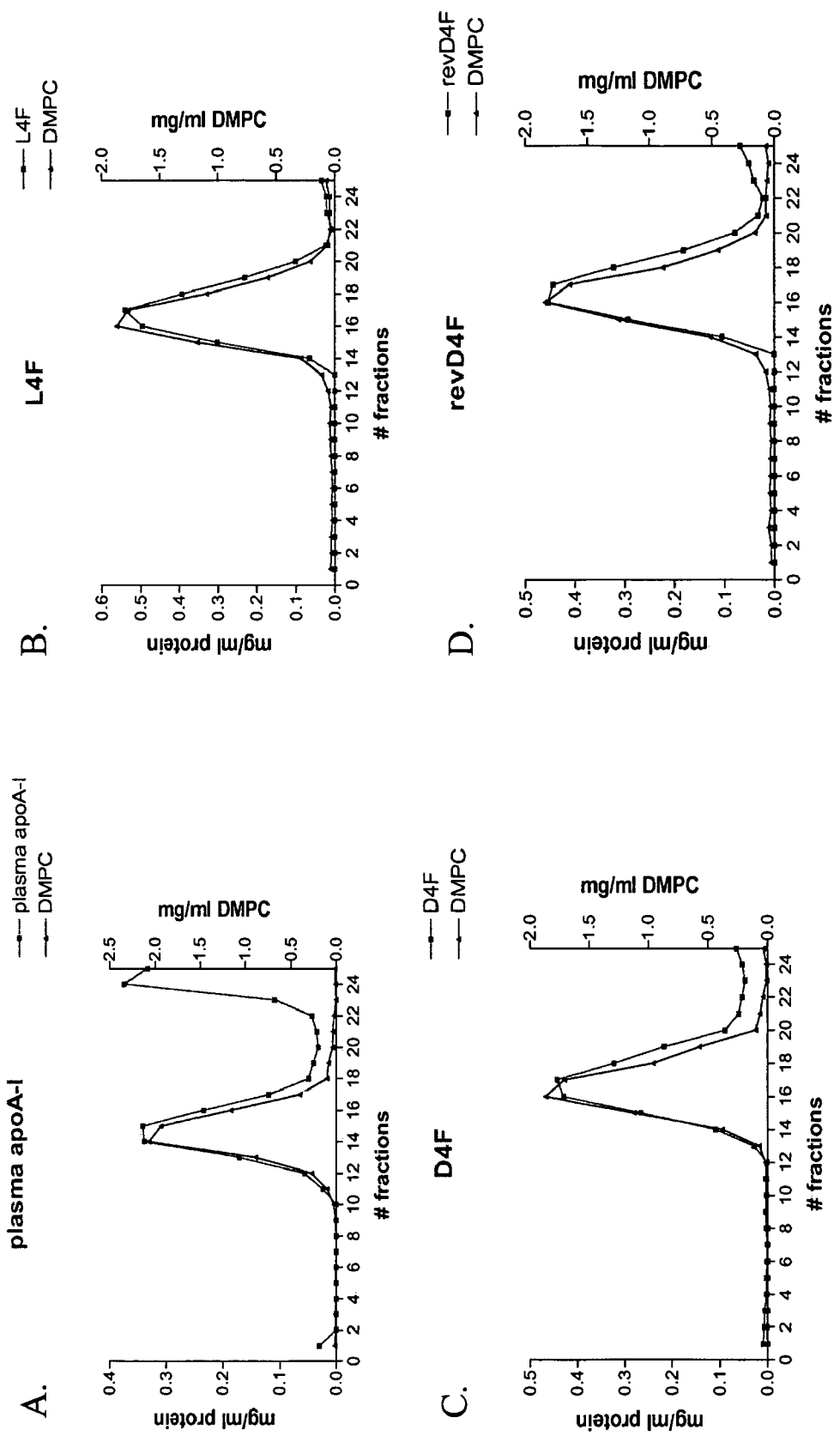
FIGS. 2A-D depict the elution profiles of $^{14}$C-labeled phospholipid and protein or peptide.

There is a strong correlation between vascular ailments and abnormal lipid parameters, such as elevated levels of cholesterol, especially LDL cholesterol in the blood and in the cardiovascular system in general and decreased HDL. Beneficially altering the lipid parameters so as to control the amounts of cholesterol within the circulating blood as well as in local foci is considered to be effective in reducing the occurrence of atherosclerosis and subsequent morbidity.

The present invention provides peptidomimetics of Apolipoprotein A-I, which is useful for altering the lipid parameters so as to beneficially influence the plasma cholesterol levels. The present invention is further generally directed to methods and compositions for treatment of abnormally elevated cholesterol levels in the cardiovascular system.

II. Definitions

The term "amino acid residue" is known in the art. In general the abbreviations used herein for designating the amino acids and the protective groups are based on recommendations of the IUPAC-IUB Commission on Biochemical Nomenclature (see *Biochemistry* (1972) 11:1726-1732). In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

As used herein, the terms "agent" and "compound" include both protein and non-protein moieties. An agent may be a small organic molecule, a polypeptide, a protein, a peptide complex, a peptidomimetic, a non-peptidyl agent, or a polynucleotide.

As used herein, "ameliorates" means alleviate, lessen, or decrease the extent of a symptom or decrease the number of occurrences of episodes of a disease manifestation.

"Apoproteins" are specialized proteins in the outer shell of lipoproteins. While different apoproteins are found in varying amounts in the lipoproteins, all play a crucial role in lipoprotein metabolism. Some apoproteins on lipoprotein particle interact with specific cell surface receptors, while others activate or deactivate enzymes involved in lipid metabolism. Ten principal apoproteins have been isolated and characterized, which are synthesized and secreted by the liver and the intestine. Certain lipoproteins comprise certain particle class. For example, Apolipoprotein ("Apo") B-100 is associated with VLDL, IDL, and LDL, whereas Apo A is associated with HDL. Apo B-100 helps remove cholesterol from the blood and Apo A helps HDL remove cholesterol from tissues.

Apo A-I is the major HDL apoprotein and is required for normal production of HDL. The precursor of most plasma HDL is a discoidal particle containing Apo A-I and phospholipids called pre-β1 HDL. Discoidal pre-β1 HDL can acquire free (unesterified) cholesterol from the cell membranes of tissues, such as arterial wall macrophages by interacting with the class B, type I scavenger receptor to which the Apo A-I of HDL docks so the free cholesterol to or from the HDL particle. After free cholesterol is acquired by pre-β1 HDL, it is esterified, nonpolarized and moves into the core of the HDL.

It is believed that "atherosclerosis" begins with an injury to the inner wall of the artery (endothelium or endothelial cells). Once the inner wall is damaged, a combination of biological processes can lead to the accumulation of the plaque. In response to the injury, macrophages accumulate at the site and migrate beneath the inner layer. The macrophages then begin to absorb fatty substances from the blood and become foam cells. An accumulation of foam cells and other substances, such as proliferating smooth muscle cells, contribute to the formation of plaque and eventually forms bulges in the artery wall. Over time, as the bulges continue to absorb fatty substances, plaque accumulations narrow the vessel lumen and occlude the blood flow. Further, plaque accumulation may cause blood vessel walls to harden and lose their elasticity, which can increase resistance to blood flow and raise blood pressure. As a result, vascular diseases are considered a progressive illness with symptoms often not evident until people are middle aged or older.

The accumulating plaque causes blockage of the blood vessel, facilitating clotting and leading to insufficient blood supply to critical body organs, which results in decreased supply of oxygen and nutrients, which results in organ failures including heart attack, stroke, or kidney failure, and causing hypertension. When atherosclerosis occurs in the coronary arteries (coronary artery disease (CAD) or coronary heart disease (CHD)) the condition may result in oxygen starvation to the heart leading to conditions such as cardiac ischemia, angina, myocardial infarction, arrhythmias and eventually in a heart attack, a major cause of morbidity and mortality in recent years. When atherosclerosis occurs in the peripheral arteries (peripheral artery disease (PAD), the condition may result in oxygen starvation to the legs muscles leading to decreased mobility and eventually to loss of mobility.

The term "$ED_{50}$" means the dose of a drug which produces 50% of its maximum response or effect.

An "effective amount" of, e.g., a peptidomimetic, with respect to the subject method of treatment, refers to an amount of the peptidomimetic in a preparation which, when applied as part of a desired dosage regimen inhibits or brings about, e.g., prevents or produces change in the rate or number of atherosclerotic lesion formation according to clinically acceptable standards for the disorder to be treated or the effect desired.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

As used herein, "inhibits" means that the amount is reduced as compared with the amount that would occur in a control sample. In a preferred embodiment, inhibits means that the amount is reduced by more than 50%, even more preferably by more than 75% or even 100%.

As used herein, "instruction material" means a document or recorded media including a written or audible instruction for the use of a pharmaceutical composition. An instruction material includes a label on a bottle, a paper inserted a box, printing on the box or carton, instructions provided by a website at an address given in any of these locations, etc.

The term "$LD_{50}$" means the dose of a drug which is lethal in 50% of test subjects.

"Lipids" are fatty substances that are insoluble in water and include fats, oils, waxes, and related compounds. They may be either made in the blood (endogenous) or ingested in the diet (exogenous). Lipids are essential for normal body function and whether produced from an exogenous or endogenous source, they must be transported and then released for use by the cells. The production, transportation and release of lipids for use by the cells is referred to as lipid metabolism. While there are several classes of lipids, two major classes are cholesterol and triglycerides. Cholesterol may be ingested in the diet and manufactured by the cells of most organs and tissues in the body, primarily in the liver. Cholesterol can be found in its free form or, more often, combined with fatty acids as what is called cholesterol esters.

Due to their insolubility in water, lipids, such as cholesterol, cannot be transported in the blood until they are packaged into special molecules called lipoproteins. Thus, cholesterol circulates in the bloodstream as particles associated with lipoproteins.

"Lipoproteins" are spherical compounds that are structured so that water-insoluble lipids are contained in a partially water-soluble shell. Depending on the type of lipoprotein, the contents include varying amounts of free and esterified cholesterol, triglycerides and apoproteins or apolipoproteins. There are five major types of lipoproteins, which differ in function and in their lipid and apoprotein content and are classified according to increasing density: (i) chylomicrons and chylomicron remnants, (ii) very low density lipoproteins ("VLDL"), (iii) intermediate-density lipoproteins ("IDL"), (iv) low-density lipoproteins ("LDL"), and (v) high-density lipoproteins ("HDL"). Cholesterol circulates in the bloodstream as particles associated with lipoproteins.

LDL becomes atherogenic when modified by oxidation, a required step for LDL uptake by the scavenger receptors of macrophages in plaque build-up, which leads to the formation of foam cells. Class A amphipathic domain of Apo A-I in mimetic peptides is responsible for its lipid associating property. Apo A-I mimetic peptides of the invention generally alter the LDL lipid parameter by removing phospholipid seeding molecules on LDL, rendering the LDL molecules resistant to oxidation by endothelial cells. Further, it is believed that Apo A-I mimetic peptides of the invention often alter the lipid parameter HDL by converting pro-inflammatory HDL to anti-inflammatory HDL by stripping oxidized cholesterol from the HDL.

The exogenous pathway for lipid metabolism describes the process by which dietary ingested triglycerides and cholesterol are transported by chylomicrons from the digestive tract to the bloodstream and, after chylomicrons deliver triglycerides to the fat and muscle cells, chylomicron remnants return the remaining cholesterol to the liver for recycling. Specifically, dietary fats enter the small intestine from the stomach and are broken down and absorbed into the lining into the lining of the small intestine where they are packaged into chylomicrons and enter the bloodstream. Once chylomicrons enter the bloodstream, most of their triglycerides are released by lipoprotein lipase, an enzyme found in the capillary walls of fat and muscle cells. The fat cells and other peripheral cells utilize the use or store most of the triglycerides. Chylomicron remnants then package the residual triglycerides and most of the dietary cholesterol and return to the liver where they are taken up by the liver cells via a specific receptor mechanism mediated by apoproteins and the chylomicron remnants are catabolized into their constituent parts. The liver uses the resulting cholesterol to form bile acids and VLDL.

The endogenous pathway for lipid metabolism describes the process by which internally synthesized cholesterol is produced, transported and released. While all cells may make cholesterol, seventy percent is synthesized in the liver thus, the discussion will focus on hepatic synthesized cholesterol. Triglycerides synthesized in the liver combine with cholesterol (either synthesized in the liver or delivered by chylomicron remnants and HDL particles) and lipoprotein to form VLDL, enter the bloodstream and are transported to peripheral cells such as fat and muscle cells. Lipoprotein lipase removes most of the triglycerides, which are used for fuel and storage, from the VLDL. After releasing the triglycerides for use by the cells, VLDL is transformed into IDL, which is either cleared from the blood by the liver or converted to LDL. LDL is cholesterol rich and delivers cholesterol to cells or is cleared from the blood. If there is excess cholesterol, it can be taken up by cells in the blood vessel wall, leading to atherosclerosis. HDL, made in the liver and small intestine, accepts excess cholesterol from the cells and returns it to the liver for removal from the body. HDL also returns cholesterol to the liver indirectly by transferring cholesterol to VLDL, IDL or LDL.

An improvement in "lipid parameters" includes one or more of a decrease in the propensity of lipoproteins to adhere to a blood vessel, a decrease in the amount of atherosclerotic plaque (even though plasma LDL and/or HDL concentrations have not significantly changed), a reduction in the oxidative potential of an HDL or LDL particle, a regression in atherosclerosis (e.g., as measured by carotid angiography or ultrasound) and a reduction in cardiac events.

A "peptidomimetic" includes any modified form of an amino acid chain, such as a phosphorylation, capping, fatty acid modification and including unnatural backbone and/or side chain structures. As described below, a peptidomimetic comprises the structural continuum between an amino acid chain and a non-peptide small molecule. Peptidomimetics generally retain a recognizable peptide-like polymer unit structure. Thus, a peptidomimetic may retain the function of binding to any target molecule that a natural peptide binds to.

The term "preventing" is art-recognized, and when used in relation to a condition, such as recurrence or onset of a disease such as hypercholesterolemia, is well understood in the art, and includes administration of a composition which reduces the frequency of, or delays the onset of, symptoms of a medical condition in a subject relative to a subject which does not receive the composition.

A "subject" or "patient" to be treated by the subject method can mean either a human or non-human animal.

As used herein, "treating" means either slowing, stopping or reversing the progression of the disorder. In a preferred embodiment, "treating" means reversing the progression to the point of eliminating the disorder.

As used herein, the term "unwanted cholesterol" means low-density lipoprotein ("LDL") cholesterol and/or a mixture of LDL and high-density lipoprotein ("HDL") cholesterol having a ratio of HDL/LDL that is undesirable for one's health. The meaning of LDL and HDL is well known in the art. In general, elevated levels of LDL cholesterol are not desirable (above 180 mg/dl), and a certain amount of HDL cholesterol (above 35 mg/dl) is beneficial to the cardiovascular health. In particular, high concentrations of LDL (above 180 mg/dl) and low concentrations of HDL (below 35 mg/dl) have been shown to be important contributors to the development of atherosclerosis. Other diseases, such as peripheral vascular disease, stroke, and hypercholesterolemia are also negatively affected by adverse HDL/LDL ratios. "Hypercholesterolemia" is generally defined as having an elevated level of total cholesterol above 200 mg/dl, especially with the LDL level above 160 mg/dl. It can be an autosomal dominant genetic disease (familial hypercholesterolemia). Hypercholesterolemia impairs vasodilation, leading to hypertension and impaired circulation. Therefore, controlling the levels of each type of the lipoproteins is effective and necessary to maintain cardiovascular health.

The terms "amine" and "amino" are art-recognized and refer to both unsubstituted and substituted amines, e.g., a moiety that can be represented by the general formula:

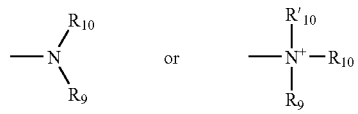

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In still more preferred embodiments, the term 'amine' does not encompass amides, e.g., wherein one of $R_9$ and $R_{10}$ represents a carbonyl. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

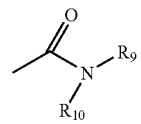

wherein $R_9$, $R_{10}$ are as defined above. Preferred embodiments of the amide will not include imides which may be unstable.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

III. Exemplary Embodiments

Compounds

Peptidomimetics are compounds based on, or derived from, peptides and proteins. The peptidomimetics of the present invention typically can be obtained by structural modification of one or more native amino acid residues, e.g., using unnatural amino acids, conformational restraints, isosteric replacement, and the like. The subject peptidomimetics constitute the continuum of structural space between peptides and non-peptide synthetic structures.

Such peptidomimetics can have such attributes as being non-hydrolyzable (e.g., increased stability against proteases or other physiological conditions which degrade the corresponding peptide copolymers), increased specificity and/or potency. For illustrative purposes, peptide analogs of the present invention can be generated using, for example, benzodiazepines (e.g., see Freidinger et al. in "Peptides: Chemistry and Biology," G. R. Marshall ed., ESCOM Publisher: Leiden, Netherlands, 1988), substituted gamma lactam rings (Garvey et al. in "Peptides: Chemistry and Biology," G. R. Marshall ed., ESCOM Publisher: Leiden, Netherlands, 1988, p 123), C-7 mimics (Huffman et al. in "Peptides: Chemistry and Biology," G. R. Marshall ed., ESCOM Publisher: Leiden, Netherlands, 1988, p. 105), keto-methylene pseudopeptides (Ewenson et al. (1986) *J. Med. Chem.* 29:295; and Ewenson et al. in "Peptides: Structure and Function (Proceedings of the 9th American Peptide Symposium)," Pierce Chemical Co. Rockland, Ill., 1985), β-turn dipeptide cores (Nagai et al. (1985) *Tetrahedron Lett.* 26:647; and Sato et al. (1986) *J. Chem. Soc. Perkin Trans.* 1: 1231), β-aminoalcohols (Gordon et al. (1985) *Biochem. Biophys. Res. Commun.* 126:419; and Dann et al. (1986) *Biochem. Biophys. Res. Commun.* 134:71), diaminoketones (Natarajan et al. (1984) *Biochem. Biophys. Res. Commun.* 124:141), and methyleneamino-modifed (Roark et al. in "Peptides: Chemistry and Biology," G. R.

Marshall ed., ESCOM Publisher: Leiden, Netherlands, 1988, p 134). Also, see generally, Session III: Analytic and synthetic methods, in "Peptides: Chemistry and Biology," G. R. Marshall ed., ESCOM Publisher: Leiden, Netherlands, 1988)

Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

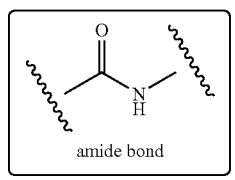

amide bond

Examples of Surrogates

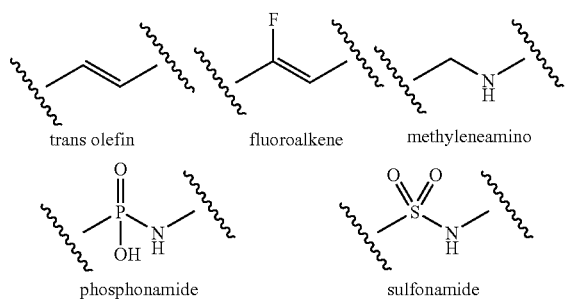

trans olefin    fluoroalkene    methyleneamino phosphonamide    sulfonamide

Additionally, peptidomimetics based on more substantial modifications of the backbone of a peptide can be used. Peptidomimetics which fall in this category include (i) retro-inverso analogs, and (ii) N-alkyl glycine analogs (so-called peptoids).

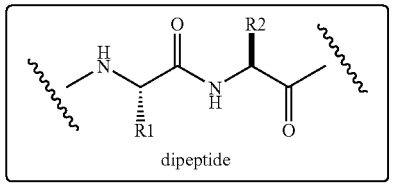

dipeptide

Examples of Analogs

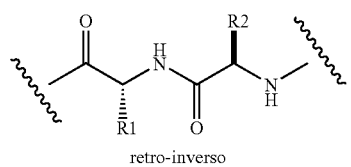

retro-inverso

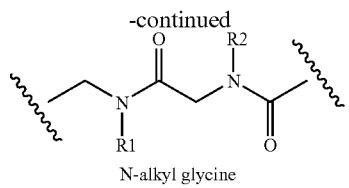

N-alkyl glycine

Furthermore, the methods of combinatorial chemistry are being brought to bear on the development of peptidomimetic copolymers. For example, one embodiment of a so-called "peptide morphing" strategy focuses on the random generation of a library of peptide analogs that comprise a wide range of peptide bond substitutes.

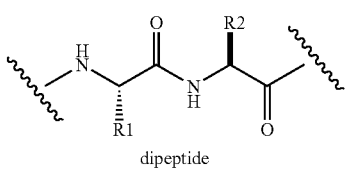

dipeptide peptide morphing

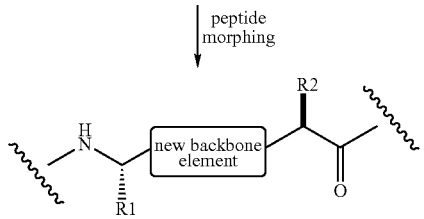

In a preferred embodiment of the present invention, the peptidomimetic is a retro-inverso analog. Retro-inverso analogs can be made according to the methods known in the art, in a manner similar to synthesizing L-amino acid based peptides. More specifically, see methods such as that described by Sisto et al. in U.S. Pat. No. 4,522,752. The final product, or intermediates thereof, can be purified by HPLC or any other suitable chromatographic method.

In another illustrative embodiment, the peptidomimetic can be derived as a retro-enantio analog. Retro-enantio analogs such as this can be synthesized from commercially available D-amino acids (or analogs thereof) and standard solid- or solution-phase peptide-synthesis techniques.

In still another illustrative embodiment, trans-olefin derivatives can be made. A trans-olefin analog of a peptide can be synthesized according to the method of Y. K. Shue et al. (1987) *Tetrahedron Lett.* 28:3225, and also according to other methods known in the art. It will be appreciated that variations in the cited procedure, or other procedures available, may be necessary according to the nature of the reagent used.

It is further possible to couple the pseudodipeptides synthesized by the above method to other pseudodipeptides, to make pseudopeptides with several olefinic functionalities in place of amide functionalities. For example, pseudodipeptides corresponding to certain di-peptide sequences could be made and then coupled together by standard techniques to yield an analog of the peptide which has alternating olefinic bonds between residues.

Still another class of peptidomimetic derivatives includes phosphonate derivatives. The synthesis of such phosphonate derivatives can be adapted from known synthesis schemes. See, for example, Loots et al. in "Peptides: Chemistry and Biology," (Escom Science Publishers, Leiden, 1988, p. 118); Petrillo et al. in "Peptides: Structure and Function (Proceedings of the 9th American Peptide Symposium)," Pierce Chemical Co. Rockland, Ill., 1985).

In other embodiments, the modification may be the introduction of carbohydrate or lipid moieties. Such modifications also change the solubility of the peptides in various mediums so that they can advantageously be prepared as a suitable pharmaceutical composition. Modifying lipid groups include farnesyl groups and myristoyl groups. Modifying carbohydrate groups include single sugars or oligosaccharides of any naturally occurring and/or synthetic sugar and sugar alcohols, for example glucose, galactose, rhamnose, mannose, arabinose, and other sugars, and their respective alcohols.

The compounds of present invention comprise at least 15 amino acid residues, and more preferably 18 amino acid residues.

In certain embodiments, the peptidomimetic of the present invention has a substantially similar three-dimensional conformation as a peptide comprising a D-amino acid sequence F-A-E-K-F-K-E-A-V-K-D-Y-F-A-K-F-W-D (SEQ ID NO:3). In particular embodiments, the peptide includes at least one backbone linkage that is not an amide linkage in the amino to carboxy direction, such as a retro-inverso peptide relative to a naturally-occurring peptide, or at least one backbone linkage that is not an amide linkage.

In an exemplary embodiment, the peptidomimetic has at least 75%, at least 80%, at least 85%, at least 90% or at least 95% identity to SEQ ID NO:3 or SEQ ID NO:2. Non-identical amino acid residues can be naturally or non-naturally occurring. The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

In another exemplary embodiment, which can overlap with the embodiments described above, the amino acids in the peptidomimetic of SEQ ID NO:3 or SEQ ID NO:2 are substituted with conservative amino acid residues. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). One example of a set of amino acid groups defined in this manner include: (i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

In a preferred embodiment, the peptidomimetic of the present invention is a retro-inverso peptide of the D-amino acid sequence:

F-A-E-K-F-K-E-A-V-K-D-Y-F-A-K-F-W-D   (SEQ ID NO:3)

wherein each letter stands for the conventional one-letter amino acid code, but of the D-amino acid.

In a more preferred embodiment, the peptidomimetic of the present invention is a retro-inverso peptide of the D-amino acid sequence:

(SEQ ID NO:2)
Ac-F-A-E-K-F-K-E-A-V-K-D-Y-F-A-K-F-W-D-NH$_2$  (I)

wherein each letter stands for the conventional one-letter amino acid code, but of the D-amino acid.

In other embodiments, the peptidomimetics of the present invention are analogs of (I) wherein one or more D-amino acid residues are substituted by other D-amino acids or other unnatural residues that, upon substitution, retain the spatial and ionic or nonionic character of the residues that they substitute.

The peptidomimetics of the present invention, including the retro-inverso peptide of (I), may be modified so that the amino and/or carboxy terminus is protected by a protecting group such as acetyl, $CH_3$—$(CH2)_n$—CO—, amide, Fmoc, t-butoxycarbonyl (t-BOC), 9-fluoreneacetyl group, 1-fluorenecarboxylic group, 9-fluorenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), cyclohexyloxy (cHxO), t-butoxymethyl (Bum), t-butoxy (tBuO), t-Butyl (tBu), and Trifluoroacetyl (TFA). The variable n is an integer from 0 to 12, typically 0 to 6 such as 0 to 4.

In certain embodiments, the peptidomimetics of the invention may further comprise modifications analogous to post-translational modifications. Such modifications include, but are not limited to, acetylation, carboxylation, glycosylation, phosphorylation, lipidation, and acylation. As a result, the modified peptidomimetics may contain non-amino acid elements, such as polyethylene glycols, lipids, poly- or mono-saccharide, and phosphates. Effects of such non-amino acid elements on the functionality of a peptidomimetic may be tested by methods such as those described in the working examples.

Therapeutic Compositions

Another aspect of the present invention provides pharmaceutical compositions comprising a pharmaceutically effective amount of a peptidomimetic of the present invention and an acceptable carrier and/or excipients. A pharmaceutically acceptable carrier includes any solvents, dispersion media, or coatings that are physiologically compatible that preferably does not interfere with or otherwise inhibit the activity of the peptidomimetic. Preferably, the carrier is suitable for intravenous, intramuscular, oral, intraperitoneal, transdermal, topical, or subcutaneous administration. One exemplary pharmaceutically acceptable carrier is physiological saline. Other pharmaceutically acceptable carriers and their formulations are well-known and generally described in, for example, *Remington's Pharmaceutical Science* (18$^{th}$ Ed., ed. Gennaro, Mack Publishing Co., Easton, Pa., 1990). Various pharmaceutically acceptable excipients are well-known in the art and can be found in, for example, *Handbook of Pharmaceutical Excipients* (4$^{th}$ ed., Ed. Rowe et al. Pharmaceutical Press, Washington, D.C.). The composition can be formulated as a solution, microemulsion, liposome, capsule, tablet, or other suitable form. The active component may be coated in a material to protect it from inactivation by the environment prior to reaching the target site of action.

In certain embodiments of the present invention, the pharmaceutical compositions are sustained release formulations. Peptidomimetics of the present invention may be admixed with biologically compatible polymers or matrices which control the release rate of the copolymers into the immediate environment. Controlled or sustained release compositions include formulation in lipophilic depots (e.g., fatty acids, waxes, oils). Also contemplated by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral. Acceptable carriers include carboxymethyl cellulose (CMC) and modified CMC.

The pharmaceutical composition of the present invention is preferably sterile and non-pyrogenic at the time of delivery, and is preferably stable under the conditions of manufacture and storage.

The compound of the present invention may be used in combination, either as separate units or fixed combinations with one or more of the following: an antibody which binds to an unwanted inflammatory molecule or cytokine such as interleukin-6, interleukin-8, granulocyte macrophage colony stimulating factor, and tumor necrosis factor-α; an enzyme inhibitor such as a protease inhibitor aprotinin or a cyclooxygenase inhibitor; an antibiotic such as amoxicillin, rifampicin, erythromycin; an antiviral agent such as acyclovir; a steroidal anti-inflammatory such as a glucocorticoid; a non-steroidal anti-inflammatory such as aspirin, ibuprofen, or acetaminophen; or a non-inflammatory cytokine such as interleukin-4 or interleukin-10. Other cytokines and growth factors such as interferon-β, tumor necrosis factors, antiangiogenic factors, erythropoietins, thrombopoietins, interleukins, maturation factors, chemotactic protein, and their variants and derivatives that retain similar physiological activities may also be used as an additional ingredient.

The compound of the present invention may also be used in combination with drugs commonly used to treat lipid disorders in diabetic patients. Such drugs include, but are not limited to, HMG-CoA reductase inhibitors, nicotinic acid, ezetimide, bile acid sequestrants fibric acid derivatives, MTP inhibitor, ACAT inhibitor and CETP inhibitors. Examples of HMG-CoA reductase inhibitors are lovastatin, pravastatin, simvastatin, rosuvastatin, fluvastatin and atorvastatin. Examples bile acid sequestrants are cholestyramine, colestipol and colesevelam. Examples of fibric acid derivatives are: gemfibrozil and fenofibrate, Peptidomimetics of the invention may also be used in combination with anti-hypertensive drugs, such as, for example, diuretics, β-blockers, cathepsin S inhibitors, methyldopa, α2-adrenergic agonists, guanadrel, reserpine, β-adrenergic receptor antagonists, α1-adrenergic receptor antagonists, hydralazine, minoxidil, calcium channel antagonists, ACE inhibitors and angiotensin II-receptor antagonists. Examples of β-blockers are acebutolol, bisoprolol, esmolol, propanolol, atenolol, labetalol, carvedilol, and metoprolol. Examples of ACE inhibitors are captopril, enalapril, lisinopril, benazepril, fosinopril, ramipril, quinapril, perindopril, trandolapril, and moexipril.

Peptidomimetics of the invention may also be used in combination with cardiovascular drugs such as calcium channel antagonists, β-adrenergic receptor antagonists and agonists, aldosterone antagonists, ACE inhibitors, angiotensin II receptor antagonists, nitrovasodilators, and cardiac glycosides.

Peptidomimetics of the invention may also be used in combination with anti-inflammatory drugs such as H1-receptor antagonists, H2-receptor mediated agonists and antagonists; COX-2 inhibitors, NSAID, salicylates, acetaminophen, propionic acid derivatives, enolic cids, diaryl substituted fuanones, cyclooxygenase inhibitors, and bradykinin agonists and antagonists.

Method of Treatment

One aspect of the present invention provides for methods to treat a subject showing the symptoms of or at risk of developing atherosclerosis by administering one or more peptidomimetic of the present invention to the subject in a therapeutically effective amount.

In general, an embodiment of the invention is to administer a suitable dose (e.g., daily dose) of a therapeutic composition that will be the lowest effective dose to produce a therapeutic effect, for example, mitigating symptoms, but consistently provide therapeutically effective in vivo levels. The therapeutic peptidomimetics are preferably administered at a dose per subject per day of at least about 2 mg, at least about 5 mg, at least about 10 mg, or at least about 20 mg as appropriate minimal starting dosages. In one embodiment of the methods described herein, a dose of about 0.01 to about 500 mg/kg can be administered. In general, the effective dosage of the compound of the present invention is about 50 to about 400 micrograms of the compound per kilogram of the subject per day. However, it is understood by one skilled in the art that the dose of the composition of the invention will vary depending on the subject and upon the particular route of administration used. It is routine in the art to adjust the dosage to suit the individual subjects. Additionally, the effective amount may be based upon, among other things, the size of the compound, the biodegradability of the compound, the bioactivity of the compound and the bioavailability of the compound. If the compound does not degrade quickly, is bioavailable and highly active, a smaller amount will be required to be effective and/or less frequent dosing may be suitable (e.g., fewer times per day, less than once per day). The actual dosage suitable for a subject can easily be determined as a routine practice by one skilled in the art, for example a physician or a veterinarian given a general starting point.

The compound may be delivered hourly, daily, weekly, monthly, yearly (e.g., in a time release form) or as a one-time delivery. The delivery may be continuous delivery for a period of time, e.g., intravenous delivery. In one embodiment of the methods described herein, the agent is administered at least once per day. In one embodiment, the agent is administered daily. In one embodiment, the agent is administered every other day. In one embodiment, the agent is administered every 6 to 8 days. In one embodiment, the agent is administered weekly.

In one embodiment of the methods described herein, the route of administration can be oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or otic delivery, or any other methods known in the art as one skilled in the art may easily perceive. Other embodiments of the compositions of the invention incorporate particulate forms protective coatings, protease inhibitors or permeation enhancers for various routes of administration, including parenteral, pulmonary, nasal and oral.

An embodiment of the method of present invention is to administer the peptidomimetic of the present invention in a sustained release form. Such method comprises applying a sustained-release transdermal patch or implanting a sustained-release capsule or a coated implantable medical device so that a therapeutically effective dose of the peptidomimetic of the present invention is continuously delivered to a subject of such a method. The compounds and/or agents of the subject invention may be delivered via a capsule which allows sustained-release of the agent or the peptide over a period of time. Controlled or sustained-release compositions include formulation in lipophilic depots (e.g., fatty acids, waxes, oils). Also contemplated by the invention are particulate compositions coated with polymers (e.g., poloxamers or poloxamines).

In another related embodiment, the methods further comprise administering at least one additional therapeutic agent. Such an agent may be an antibody, an enzyme inhibitor, an antibacterial agent, an antiviral agent, a steroid, a nonsteroidal anti-inflammatory agent, an antimetabolite, a cytokine, or a soluble cytokine receptor. The enzyme inhibitor may be a protease inhibitor or a cyclooxygenase inhibitor. The additional agent may be added as a part of the pharmaceutical composition, or may be administered concomitantly or within a time period when the physiological effect of the additional agent overlaps with the physiological effect of the compound of the present invention. More specifically, an additional agent may be administered concomitantly or one week, several days, 24 hours, 8 hours, or immediately before the administration of the copolymer. Alternatively, an additional agent may be administered one week, several days, 24 hours, 8 hours, or immediately after the administration of the copolymer.

Another embodiment of the present invention is a method for prophylactically treating a subject at risk of developing an autoimmune disease by administering a compound of the present invention. A subject at risk is identified, for example, based on familial history, or any genetic markers that correlate with atherosclerosis. Such prophylactic treatment may additionally comprise other pharmaceutical agents.

Research Tools

The peptidomimetics of the invention are also useful as research tools. For example, the peptidomimetics of the invention can be used to evaluate the anti-atherosclerotic potential of other compounds (including other peptidomimetics).

In addition, peptidomimetics of the invention can be used for investigating lipoprotein-receptor interactions in animals and animal models, particularly when a peptidomimetic is labeled (e.g., radioactive label, fluorescent label).

The peptidomimetics of the invention can also be used to identify appropriate animal models for elucidation of lipid metabolic pathways. For example, the peptidomimetics can be used to identify animal models where lipid peroxidation contributes to the progression of atherosclerosis.

IV. EXAMPLES

Example 1.

Synthesis and Purification of a Retro-Inverso Peptidomimetic Rev-D4F

The retro-inverso peptidomimetic Rev-D4F was synthesized using a standard peptide synthesis method and purified by high performance liquid chromatography.

To assess the ability of purified Rev-D4F to interact with phospholipids, the purified peptidomimetic was mixed with 1,2-dimyristoyl-sn-glycero-3-phosphocholine (DMPC), which is a component of membrane lipid bi-layer with which cholesterol is associated, and fractionated by gel filtration chromatography. Rev-D4F, similarly to L4F and D4F, associated spontaneously with DMPC efficiently, and all of the peptidomimetic co-eluted with the phospholipid (FIGS. 2B-D). In contrast, only certain portions of intact Apo A-I protein associates with the phospholipid spontaneously (FIG. 2A).

Example 2.

Effect of Rev-D4F on SR-BI-Dependent Cholesterol Efflux

The effect of Rev-D4F on the cholesterol efflux in a receptor-manner was examined. Scavenger receptor class B type I ("SR-BI") is a receptor for HDL normally expressed on the surface of the liver cells. Tritiated cholesterol was added to cells transfected with SR-BI, with wild type Apo A-I, L4F peptide, D4F peptide, or Rev-D4F peptidomimetic, and the percentage of cholesterol efflux was determined.

Figure 3:
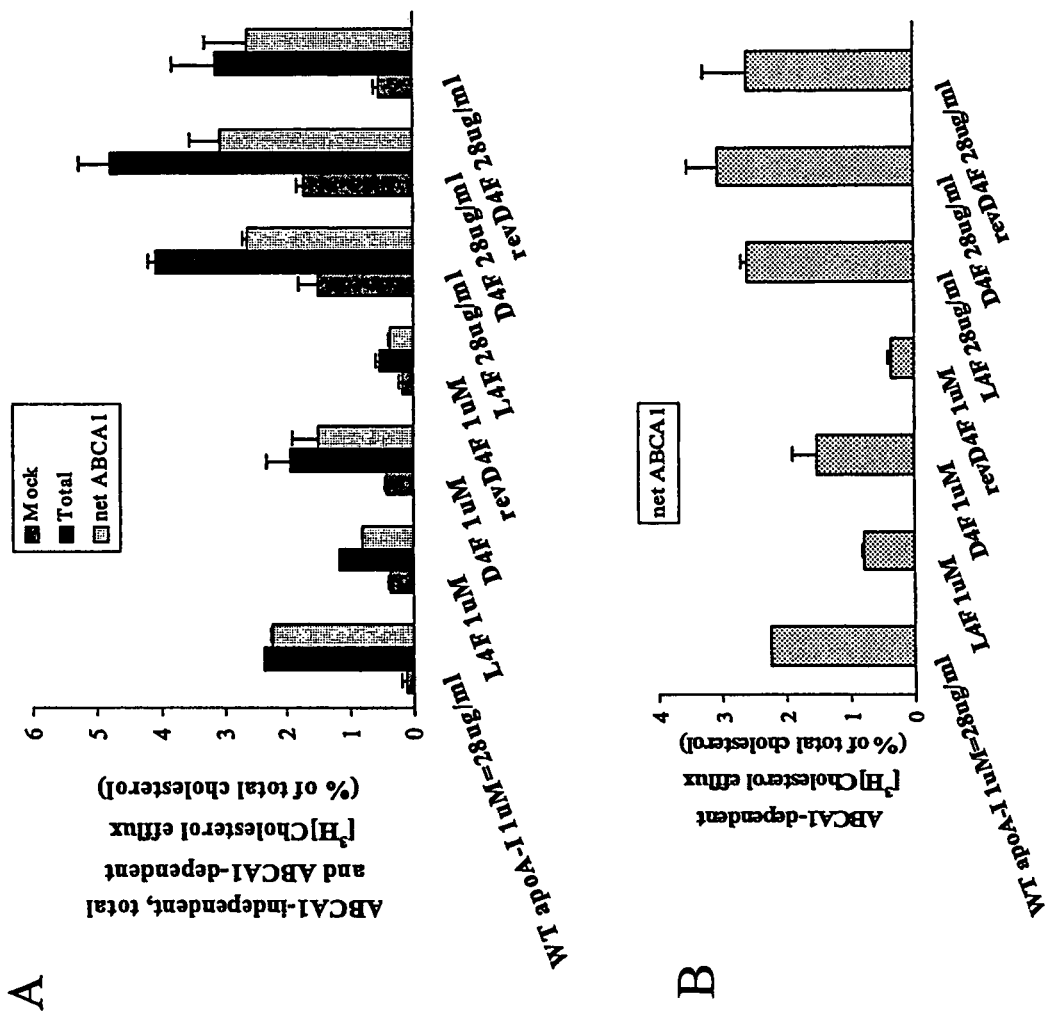
FIGS. 3A and B depict the ability of lipid bound peptides and Apo A-I to promote SR-BI-dependent cholesterol efflux.

When compared to Apo A-I on a per weight basis, L4F, D4F, and Rev-D4F all were more efficient in promoting efflux than Apo A-I protein. When compared on per mole basis, all mimetic peptides were less efficient than Apo A-I protein (see FIGS. 3A and B.

Example 3.

Effect of Rev-D4F on ABCA1-Dependent Cholesterol Efflux

Figure 4:
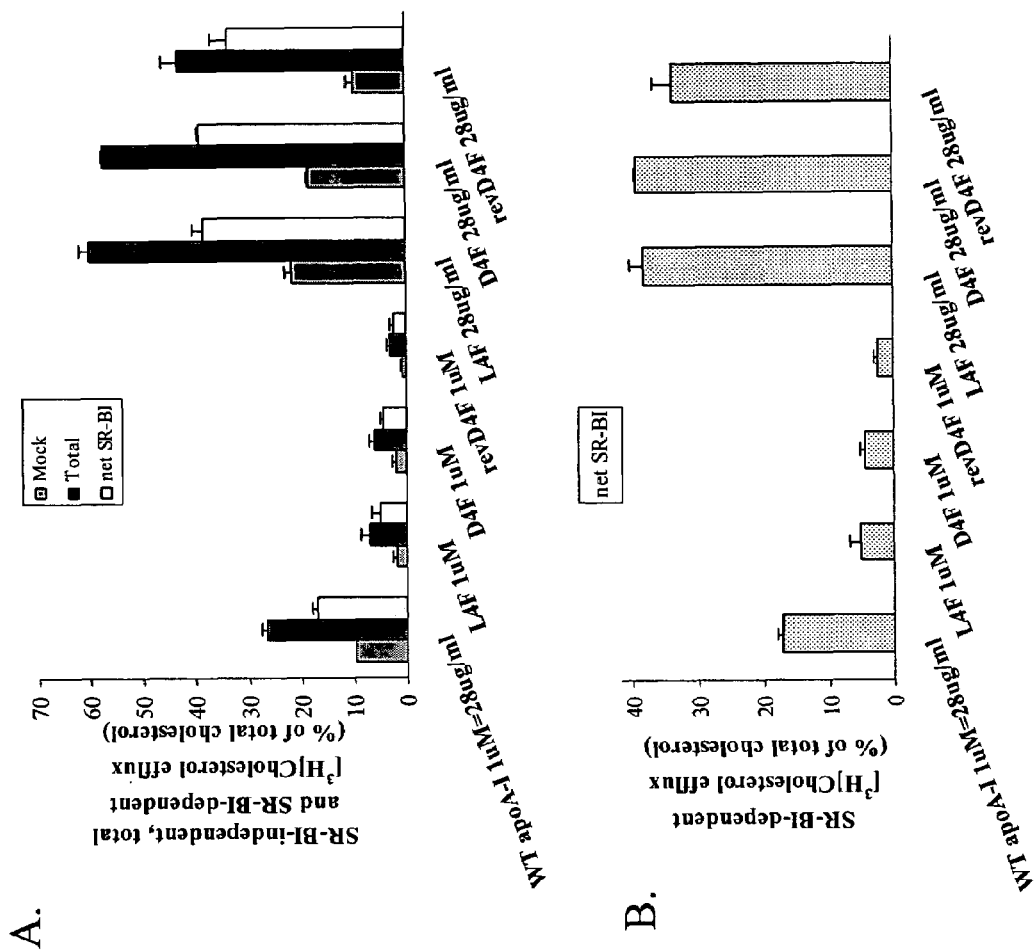
FIGS. 4A and B depict the ability of lipid-free peptides and Apo A-I to promote ABCA1-dependent cholesterol efflux.

The effect of Rev-D4F on the cholesterol efflux in a manner dependent on ATP-binding cassette protein A1 ("ABCA1") was also examined using the same methodology as for SR-BI, except that ABCA1 was transfected. Similarly to SR-BI-dependent cholesterol efflux, L4F, D4F, and Rev-D4F all were more efficient in promoting cholesterol efflux than Apo A-I on per weight basis. Also similarly to SR-BI-dependent efflux, all three were less efficient than Apo A-I when compared on per mole basis (see FIGS. 4A and B).

Example 4.

Effect of Peptidomimetics on Plasma Lipid Oxidation

Figure 5:
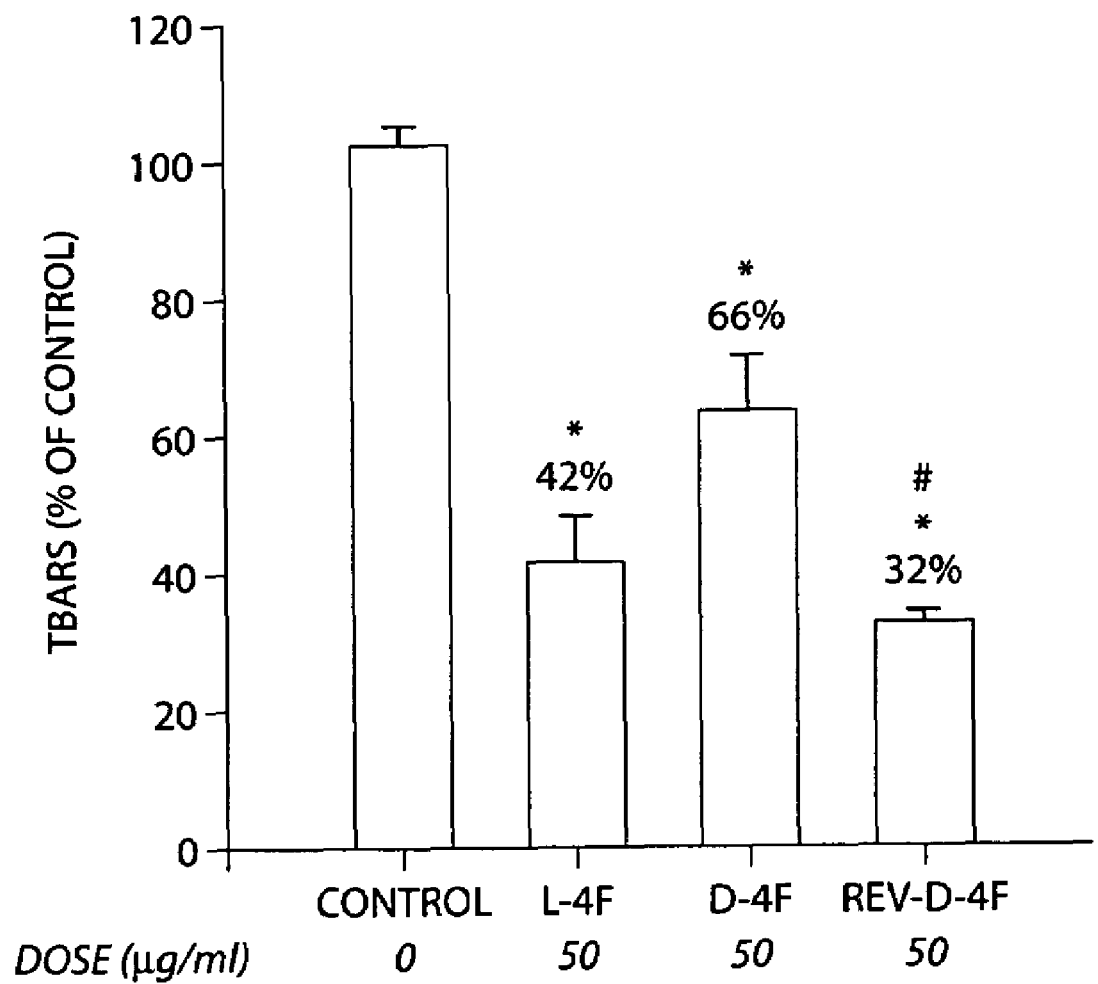
FIG. 5 shows that the peptidomimetics L-4F, D-4F and Rev D4-F inhibit lipid peroxidation caused by endothelial cells.
Figure 6:
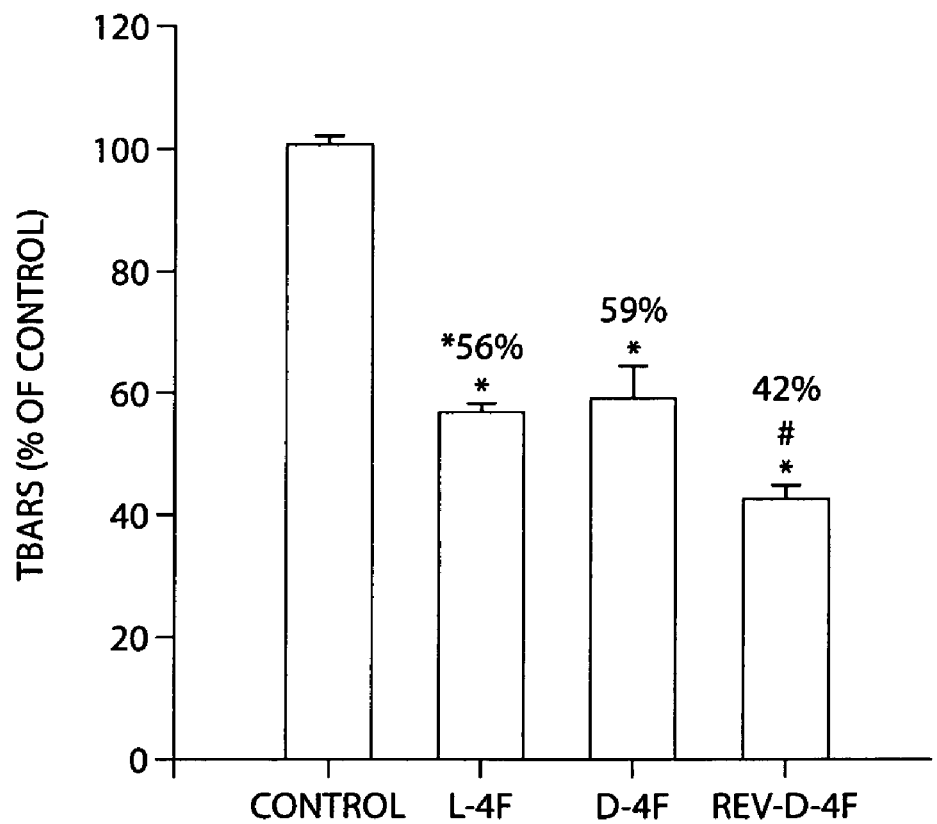
FIG. 6 shows that the peptidomimetics L-4F, D4F and Rev D4-F inhibit lipid peroxidation caused by copper sulfate.
Figure 7:
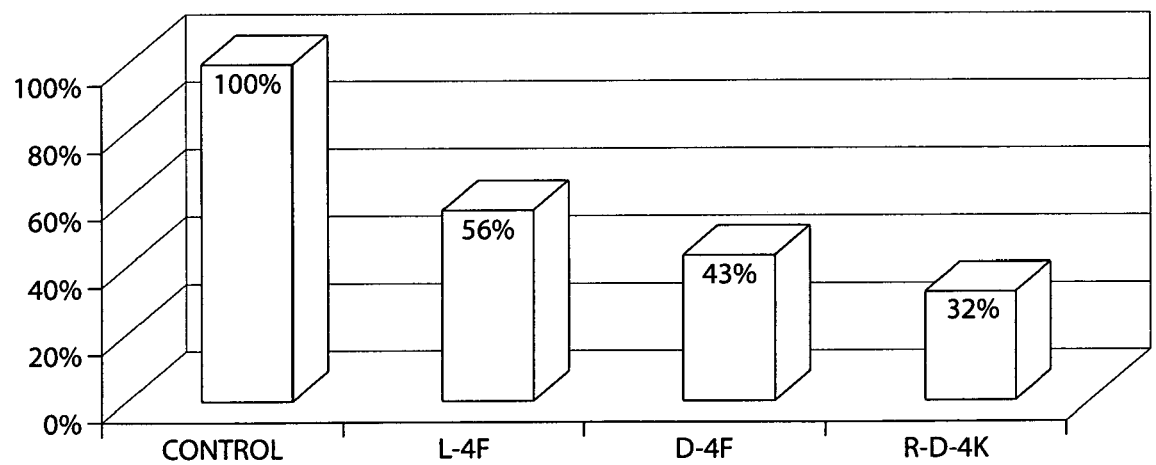
FIG. 7 shows that the peptidomimetics L-4F, D-4F and Rev D4-F inhibit MCP-1 mRNA expression in endothelial cells.

The present study measured the ability of Rev-D4F, D-4F, and L-4F mimetic peptides to inhibit lipid peroxidation caused by human aortic endothelial cells and copper(II) sulfate, based upon inhibiting an increase in concentrations of thiobarbituric acid-reactive substances (TBARS). As shown in FIGS. 5 and 6, all three mimetics significantly decreased the amount of lipid peroxidation in the presence of an oxidant. Moreover, the inhibition in lipid peroxidation associated with Rev-D4F was significantly greater than the inhibition associated with D-4F.

Example 5.

Effect of Peptidomimetics on MCP-1 mRNA Expression

This study analyzed the effects of Rev-D4F, D-4F, and L-4F mimetic peptides to reduce the levels of an anti-inflammatory marker, monocyte chemotactic protein-I (MCP-1). Based upon levels of MCP-1 mRNA, all three peptidomimetics reduced the amount of MCP-1.

Example 6.

Effect of Rev-D4F on ApoE-Null Mice

In this study, the comparative effect of Rev-D4F, D-4F, and L4F mimetic peptides on atherosclerosis in apoE-null mice was measured. Four groups of apoE-null mice (4 weeks old, n=15) were fed a chow diet, and administered water (control), Rev-D4F, D-4F, or L-4F mimetic peptides (1.6 mg/day, n=12/group) orally in drinking water for 6 weeks. Quantitative morphometry of aortic root cross sections stained with oil-red O was performed with NIH software.

Apo-AI mimetic peptides did not affect plasma total cholesterol, HDL-cholesterol, and non-HDL-cholesterol levels. L-4F had no effect on atherosclerotic lesions. Both Rev-D4F and D4F significantly ($p<0.02$) decreased lesion area by 46% and 33% respectively as compared to water control. The data indicate that Rev-D4F is at least as effective or more effective than D-4F in preventing atherosclerosis at early stages of lesion formation in apoE-null mice.

Equivalents

Contemplated equivalents of the peptidomimetics, sub-units thereof and other compositions described above include such materials which otherwise correspond thereto, and which have the same general properties thereof (e.g., biocompatible), wherein one or more simple variations of substituents are made which do not adversely affect the efficacy of such molecule to achieve its intended purpose. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are themselves known, but are not mentioned here.

All of the above-cited references are hereby incorporated by reference in their entireties.

I claim:

1. A peptidomimetic comprising the amino acid sequence F-A-E-K-F-K-E-A-V-K-D-Y-F-A-K-F-W-D (SEQ ID NO:3), wherein said peptidomimetic comprises all D-amino acid residues.

2. A peptidomimetic comprising the amino acid sequence F-A-E-K-F-K-E-A-V-K-D-Y-F-A-K-F-W-D (SEQ ID NO:3) or an amino acid sequence having only conservative amino acid substitutions therefor.

3. A peptidomimetic comprising the amino acid sequence Ac-F-A-E-K-F-K-E-A-V-K-D-Y-F-A-K-F-W-D-NH$_2$ (SEQ ID NO:2).

4. A pharmaceutical composition for the treatment of elevated levels of plasma cholesterol in a mammal, comprising a therapeutically effective amount of a peptidomimetic comprising the amino acid sequence F-A-E-K-F-K-E-A-V-K-D-Y-F-A-K-F-W-D (SEQ ID NO:3).

5. The pharmaceutical composition according to claim 4, further comprising an active agent in combination with said peptidomimetic.

* * * * *